(12) United States Patent  (10) Patent No.: US 8,585,283 B1
Doyle et al.  (45) Date of Patent: Nov. 19, 2013

(54) REAL-TIME EVALUATION OF CHANGE IN THERMAL CONDUCTIVITY ACROSS AN INTERFACE

(75) Inventors: Derek Doyle, Albuquerque, NM (US); Derek Hengeveld, Albuquerque, NM (US)

(73) Assignee: The United States of America as Represented by the Secretary of the Air Force, Washington, DC (US)

( * ) Notice: Subject to any disclaimer, the term of this patent is extended or adjusted under 35 U.S.C. 154(b) by 89 days.

(21) Appl. No.: 13/437,799

(22) Filed: Apr. 2, 2012

(51) Int. Cl.
*G01N 25/18* (2006.01)
*G01N 25/20* (2006.01)

(52) U.S. Cl.
USPC .............................................. 374/44; 374/43

(58) Field of Classification Search
USPC ...................................................... 374/44, 43
See application file for complete search history.

(56) References Cited

U.S. PATENT DOCUMENTS

| | | | |
|---|---|---|---|
| 7,034,660 B2* | 4/2006 | Watters et al. ............. | 340/10.41 |
| 7,921,727 B2* | 4/2011 | Rice ................................. | 73/762 |
| 8,347,722 B2* | 1/2013 | Qing et al. ........................ | 73/587 |
| 2005/0061076 A1* | 3/2005 | Kim ................................. | 73/587 |
| 2006/0051884 A1* | 3/2006 | McNamara et al. ............. | 438/14 |
| 2011/0138918 A1* | 6/2011 | Zagrai et al. .................... | 73/588 |
| 2011/0222225 A1* | 9/2011 | Kessler et al. ........... | 361/679.02 |
| 2012/0207188 A1* | 8/2012 | Hauser et al. .................... | 374/44 |
| 2012/0280414 A1* | 11/2012 | Giurgiutiu et al. ........... | 264/40.1 |
| 2012/0315447 A1* | 12/2012 | Ashikaga et al. .......... | 428/195.1 |
| 2013/0129275 A1* | 5/2013 | Giurgiutiu et al. .............. | 385/12 |

FOREIGN PATENT DOCUMENTS

DE 10115973 A1 * 10/2002 ............. G01N 25/18

OTHER PUBLICATIONS

Arritt et al., "Structural Health Monitoring; an Enabler for Responsive Satellites", Proc. SPIE, vol. 6935 (Mar. 10, 2008).
Argatov et al., "Health Monitoring of Bolted Joints via Electrical Conductivity Measurements", International Journal of Engineering Science, Jun. 26, 2010.

\* cited by examiner

*Primary Examiner* — Lisa Caputo
*Assistant Examiner* — Jamel Williams
(74) *Attorney, Agent, or Firm* — James M. Skorich

(57) ABSTRACT

A method of using Structural Health Monitoring (SHM) techniques for determining whether changes in thermal conductivity have occurred to a particular interface between two joined structural members is described, which is particularly useful in satellites or other structures ordinarily subjected to vacuum pressure.

8 Claims, 6 Drawing Sheets

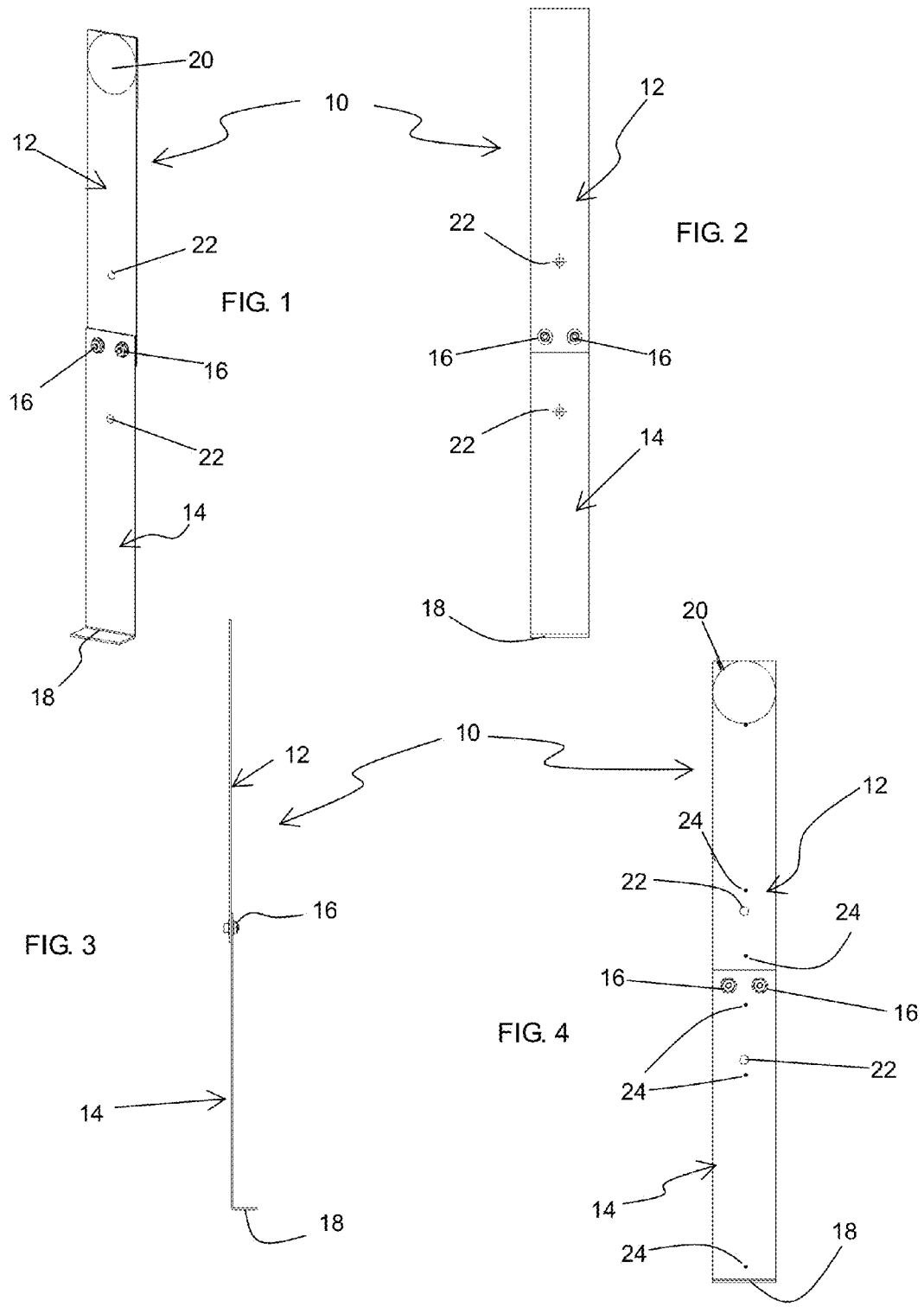

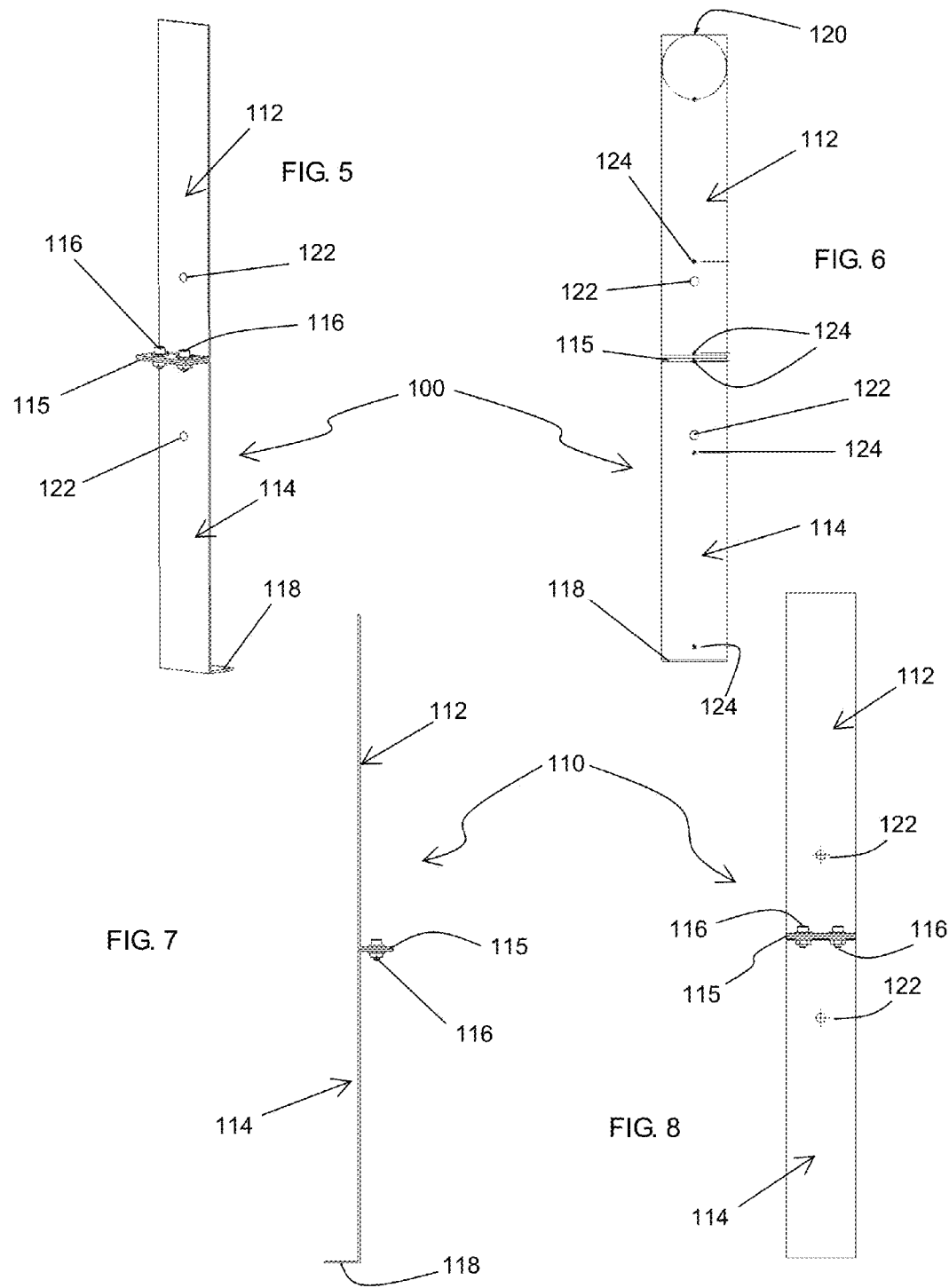

Measured Lamb Wave in Atmosphere and Vacuum.

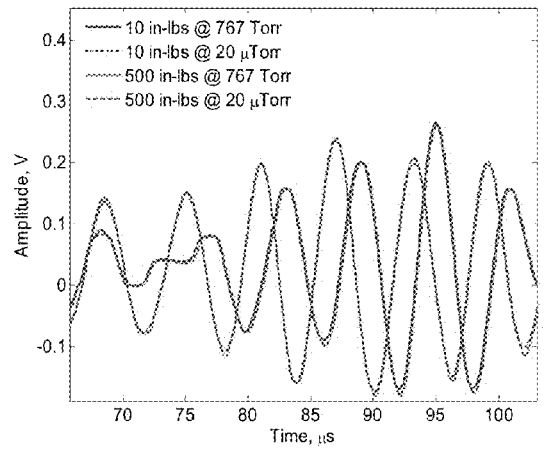

Recorded Lamb Wave in Atmosphere and Vacuum for Bolted Beam.

FIG. 11

Table 1. Summary of Experimental Procedure.

| | Bolt Torque [in-lb] | Heater Power [W] | Cold Plate Temperature [°C] | Pressure [---] |
|---|---|---|---|---|
| Test 1 | 0 (finger tight) | 4.7 | 10.0 | Ambient (bell jar open) |
| Test 2 | 0 (finger tight) | 4.7 | 10.0 | Ambient (bell jar closed) |
| Test 3 | 0 (finger tight) | 4.7 | 10.0 | Vacuum |
| Test 4 | 10 | 4.7 | 10.0 | Ambient (bell jar open) |
| Test 5 | 10 | 4.7 | 10.0 | Ambient (bell jar closed) |
| Test 6 | 10 | 4.7 | 10.0 | Vacuum |
| Test 7 | 30 | 4.7 | 10.0 | Ambient (bell jar open) |
| Test 8 | 30 | 4.7 | 10.0 | Ambient (bell jar closed) |
| Test 9 | 30 | 4.7 | 10.0 | Vacuum |
| Test 7 | 50 | 4.7 | 10.0 | Ambient (bell jar open) |
| Test 8 | 50 | 4.7 | 10.0 | Ambient (bell jar closed) |
| Test 9 | 50 | 4.7 | 10.0 | Vacuum |

FIG. 12

Measured Waveforms in Vacuum (left) and Normalized Derived Thermal Resistance of SHM and TVac Results (right)

REAL-TIME EVALUATION OF CHANGE IN THERMAL CONDUCTIVITY ACROSS AN INTERFACE

The conditions under which this invention was made are such as to entitle the Government of the United States under paragraph 1(a) of Executive Order 10096, as represented by the Secretary of the Air Force, to the entire right, title and interest therein, including foreign rights.

FIELD OF THE INVENTION

This invention relates generally to the evaluation of thermal conductivity across structural interfaces, and more particularly to systems and methods for performing such evaluations using Structural Health Monitoring (SHM) techniques.

BACKGROUND OF THE INVENTION

Current satellite pre-operational timelines can range from years to over a decade, depending upon the complexity and scope of a given system and its mission. For new concepts, this is incompatible with requirements to operate in space in a more responsive fashion. The extended developmental timeline results in obsolescence and cost/schedule increases of satellites, and since most satellites are unique and "one of a kind", they require case-specific design, analysis, and qualification. With significantly shorter proposed timelines for responsive missions, there is little to no time available for design/assembly errors to be inferred from failed environmental testing. These tests typically include component and system exposure to thermal vacuum cycling, random vibration and shock loads, and flash x-ray. Realistically, an ideal responsive schedule comprises building modular systems from qualified components in such a way that few structural interfaces between connected validated components would exist as a source of uncertainty. These final interfaces then are the only areas in need of structural qualification.

Extensive research, specifically on feature extraction for satellite interfaces, has been explored and demonstrated using Structural Health Monitoring (SHM) systems and techniques as an enabling technology for responsive goals. Research has proven the feasibility of using embedded piezoelectric wafer active sensors (PWAS) to detect, localize, and quantify preload loss at bolted interfaces in a non-destructive manner. These kinds of systems are disclosed in, for example, U.S. Patent Application Publication No. 2011/0138918, "Structural Health Monitoring; an Enabler for Responsive Satellites", Arritt et al., *Proc. SPIE*, Vol. 6935 (Mar. 10, 2008), and "Health Monitoring of Bolted Joints via Electrical Conductivity Measurements", Argatov et al., *International Journal of Engineering Science*, Jun. 26, 2010. All of these documents are herein expressly incorporated by reference, in their entirety. One particular method uses piezoelectric wafers to both excite an elastic wave and to receive it. Two of these wafers are bonded to a structure. The source piezo is excited with an electric pulse which converts the electrical signal into mechanical displacement and creates a pressure and shear wave in the substrate that propagates radially outwardly from the center of the piezo. As the wave interacts with a feature (crack, hole, edge, thickness change, interface, stressed region, etc.), the waveform will change in amplitude, shape, or frequency. When the wave reaches the second piezo sensor, the wave is converted back into an electrical signal. If some change has occurred in the structure, the new wave propagation signal will show a proportionate change from the baseline signal.

Thermal conductance for space applications can currently only be accurately measured in a thermal vacuum chamber, and requires that no atmosphere be present. Heat sources and sinks are used to create thermal gradients across an area of interest. Thermal sensors are then placed along the path of thermal transition of interest to evaluate the change of temperature across the region and define the thermal gradient for that region. These measurements are done on both sides of an interface, as close as possible to that interface to verify that the thermal gradient across that interface is within acceptance of that required for thermal management. This test can take weeks to months and cost thousands of dollars.

What is needed, therefore, is a system and method for evaluating thermal conductance for space applications without the need to create an evacuated environment, with its attendant costs and delays.

SUMMARY OF THE INVENTION

Research has been underway by the assignee of the present patent application to determine ways of using SHM methods for truncating schedules associated with the assembly, integration, and testing (AI&T) phase of satellite development without significantly reducing system reliability and incurring unacceptable mission risk. One particular test during this phase, as noted above, is the thermal/vacuum test which requires a satellite to be placed in a vacuum chamber and pumped down to near zero atmospheres and thermally cycled to evaluate the system's design and performance. Atmosphere needs to be removed to simulate the space environment, meaning that no convection can take place. One of the largest variables in this test in conductivity across interfaces is that there is no equation to currently define this value for models where non-uniform pressure distributions exist. These non-uniform pressure distributions exist wherever a bolted interface is used. This testing can be expensive and take days to weeks to perform. Research has shown that certain SHM techniques can be used to evaluate interface characteristics and detect changes in features associated with thermal conductivity. As an example, ultrasonic elastic waves excited into a surface will travel through an interface (like a bolted joint) and the features of the passing wave will be influenced by the characteristics of that joint. Vacuum is not required either in this scenario since the impedance mismatch between the solid and the atmosphere prevents energy from leaking into the atmosphere. If the stiffness of the joint is changed, then there is a measurable change in the wave transmission through the joint. Applicants have discovered that this change can be used to infer a change in thermal conductivity.

Thus, the purpose of the present invention is to identify a method to determine, in real-time, if there has been some change to a structure such that thermal conductance has changed at a critical location, and to identify the magnitude of that change. Change in thermal conductance across an interface, as noted above, can impact the performance of that structure in a space environment where thermal cycling requires proper thermal management. If during shipping or storage or launch some concerning event occurs, Applicants have devised and developed methods, using SHM techniques, to evaluate structural interfaces for a change in features that correlate to a change in thermal conductance.

Applicants have observed, in particular, that the same features that dictate thermal conductivity (surface roughness, pressure, contact area, etc.) also affect ultrasonic wave transmission. However, the real discovery is that one does not need to remove the variable of atmospheric pressure (atmosphere)

for SHM measurements. For thermal measurements, heat transfers by convection, conduction, or radiation. In space, there is no convection, meaning that, for design purposes and modeling, it is necessary to measure in a relevant embodiment (i.e. in a vacuum). However, Applicants have determined that for SHM, the elastic energy stays in the solid material, since the impedance is so great between air and the surface material. Also, in the case of thermal measurements, one must wait for hours to achieve thermal equilibrium necessary for reliable measurements. However, SHM measurements take only seconds.

More particularly, there is disclosed a method of using Structural Health Monitoring (SHM) techniques for determining whether changes in thermal conductivity characteristics have occurred to a particular interface between two joined structural members. The method comprises the steps of sending a guided wave through a structure that contains at least two structural members joined at an interface, wherein the guided wave is transmitted across the interface, measuring the guided wave that has subsequently propagated through the structure and across the interface, thus obtaining a measured result, and comparing the measured result to a baseline result previously obtained for the interface or a substantially equivalent interface, and calculating a quantitative difference between the measured result and the baseline result. Then a further step involves calculating a change in thermal conductivity across the interface which is equivalent to the quantitative difference between the measured result and the baseline result, using a predetermined algorithm.

In currently preferred embodiments, the measuring step is performed using PWAS, which detect and transmit guided wave signals to a digitizer for processing. A plurality of PWAS are disposed on each member of the structure for detecting guided wave signals. The interface comprises a bolted joint.

In another aspect of the invention, there is disclosed a method of using Structural Health Monitoring (SHM) techniques for determining whether changes in thermal conductivity characteristics have occurred to a particular interface between two joined structural members. The method comprises steps of sending a guided wave through a structure that contains at least two structural members joined at an interface, wherein the guided wave is transmitted across the interface, measuring the guided wave that has subsequently propagated through the structure and across the interface, thus obtaining a first measured result, sending a second guided wave through the interface of the structure at a point substantially later in time than the first sending step, and measuring the guided wave that has subsequently propagated through the structure and across the interface, thus obtaining a second measured result. Then a further step comprises comparing the second measured result to the first measured result and calculating a quantitative difference between the second measured result and the first measured result, following which, the inventive method comprises a step of calculating a change in thermal conductivity across the interface which is equivalent to the quantitative difference between the second measured result and the first measured result, using a predetermined algorithm.

In currently preferred embodiments, the measuring step is performed using PWAS, which detect and transmit guided wave signals to a digitizer for processing. A plurality of PWAS are disposed on each member of the structure for detecting guided wave signals. The interface comprises a bolted joint.

The invention, together with additional features and advantages thereof, may be best understood by reference to the following description taken in conjunction with the accompanying illustrative drawings. In these accompanying drawings, like reference numerals designate like parts throughout the figures.

BRIEF DESCRIPTION OF THE DRAWINGS

FIG. 1 is an isometric view of a structure to be evaluated using the methods of the present invention, having two portions and a lap joint for securing the two portions together;

FIG. 2 is a rear view of the structure of FIG. 1;

FIG. 3 is a side view of the structure of FIGS. 1-2;

FIG. 4 is a front view of the structure of FIGS. 1-3;

FIG. 5 is an isometric view of a modified structure of the type shown in FIG. 1, wherein the joint between the two portions is a flange joint;

FIG. 6 is a front view of the structure of FIG. 5;

FIG. 7 is a side view of the structure of FIGS. 5 and 6;

FIG. 8 is a rear view of the structure of FIGS. 5-7;

FIG. 11 is a graph showing the recorded Lamb Wave in atmosphere and vacuum for a bolted beam and shows data for when the joint is preloaded at two different bolt torque loads separated by an extreme range to allow clear visual distinction of feature changes that occur;

FIG. 12 is a table reporting tests performed and the environmental conditions of the test sample;

DETAILED DESCRIPTION OF THE INVENTION

Figure 9:
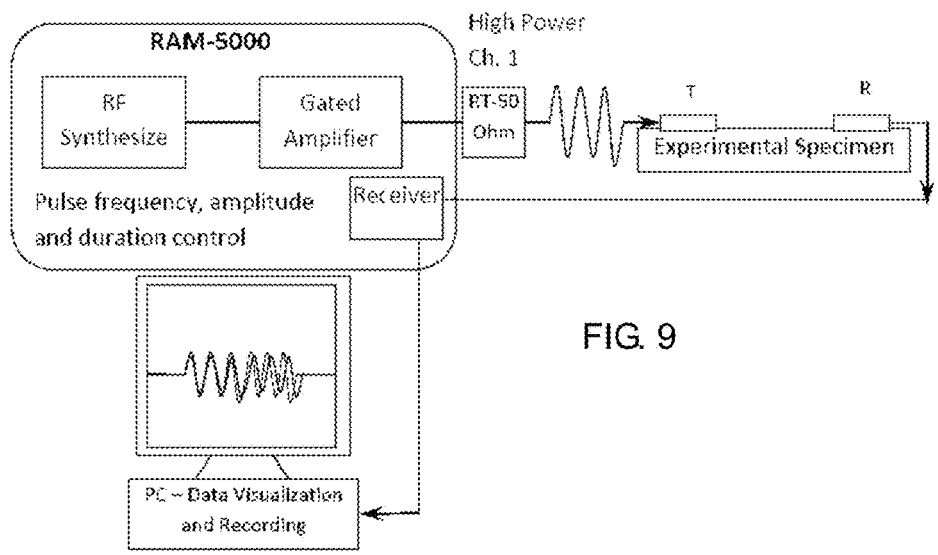
FIG. 9 is a schematic diagram of one potential apparatus setup which may be used to perform SHM evaluations in accordance with the principles of the present invention.

Now, referring more particularly to the drawings, there is shown in FIGS. 1-4 a first embodiment of a jointed assembly or structure 10 which comprises a first segment 12 joined to a second segment 14 by a lap joint secured by bolts 16. In one particular configuration, each segment 12, 14 comprised an 11 in.×2 in. strip of 1/16 in. thick 6061-T6 aluminum. The ends of each of the segments 12, 14 were drilled and bolted together using 1/4 in. bolts 16. The bolted joint was positioned such that the two strips 12, 14 had an overlap of about 1 in., giving a total surface contact area of 2 in$^2$.

In FIGS. 5-8, a somewhat modified embodiment of the structure 110 is shown, comprising segments 112, 114, wherein ends of both segments 112, 114 are bent at a 90 degree angle and joined together to form a flanged joint 115, using two bolts 116, having an overlap of 1 in. and a total surface contact area of about 2 in$^2$. In each specimen 10, 110, a folded lip 18, 118 is also bent to an angle of about 90 degrees, to allow the structure 10, 110 to be set up vertically inside a bell jar vacuum system, and to allow the folded lip 18, 118 of each structure as an interface to clamp against a cold plate, as will be described in more detail below. In the illustrated embodiments, the folded lip 18, 118 is also about 1 in. in length, to allow for approximately 2 in$^2$ of surface area to be mated with the cold plate.

Once each of the structures 10, 110 is structurally complete, each is thoroughly cleaned with a suitable cleaning solvent, such as isopropanol. Each jointed structure 10, 110 is then appropriately instrumented. The instrumentation includes a patch heater 20, 120, which may comprise, in one particular embodiment, an ultra-thin polyimide heat film, having a 2 in. diameter at 20 W/in2 (31 W), and operating at 4.695 W. However, any resistive element, through which electrical current may be directed to create heat, may be used. Preferably, actuation of the heater 20, 120 will increase the temperature at the patch to about 80 degrees C.

As noted above, a sink or cold plate (not shown) is secured to the folded lip 18, 118 of each structure 10, 110. In one particular embodiment, the cold plate may be an aluminum block with a copper coil running through it which circulates cold water. Thus, the temperature at the location 18, 118 on the structure 10, 110 is brought to the temperature of the water flowing through the cold plate, once thermal equilibrium has been achieved, which in one embodiment may be about 10 degrees C.

A plurality of piezoelectric wafer active sensors (PWAS) 22, 122 are bonded to each structure 10, 110, above and below the jointed interface, as shown. Thermocouples 24, 124 are then also attached to each structure 10, 110. One thermocouple 24, 124 is disposed above and below each jointed interface, one next to each PWAS 22, 122, and one next to each of the heating and cooling elements, as illustrated.

In an exemplary embodiment, the PWAS 22, 122 were procured from APC International, and made from PZT 850 stock. The adhesive implemented in testing to permanently bond PWAS was M-Bond 200. PWAS were excited with a 50 Vpp 325 kHz four-count pulse using a RITEC Ram 5000 system and lab computer, as shown schematically, for example, in FIG. 9. Waveforms that interact with the receiving PWAS were measured using a NI PXI digitizer. Consideration was used, when selecting a digitizer to acquire a card with high resolution and sampling rate to record clear data with adequate points per wave. Methods that rely on baseline comparison of waveforms may measure variations that are within noise limits of acquisition. The thermocouples 24 may be Omega Type E thermocouples, having an accuracy of ±2° F. at 392° F. In the illustrated embodiment, they were kapton taped to the structure along the thermal path to identify the thermal gradient, and measurements were taken up to the joint and then across the joint. Number and placement of the sensors is not critical, but design matters depending upon the resolution of thermal data points desired. A DC power source was provided, delivering 31.3V and 0.15 A. An RTE 7 refrigerated bath, set to 10° C. was provided to function as the cold plate. A Bell Jar vacuum system was provided to pump the atmospheric pressure down to below 9E-5 Torr.

The foregoing embodiment elements are exemplary only, and not critical to the functioning of the testing to be described below. Suitable alternative equivalent sensors or instrumentation, known in the art, may be substituted freely without impacting the gist of the present invention.

In the testing performed by the inventors to substantiate the validity of the inventive methods described herein, a simple structure with no interfaces (not shown) was initially examined, to verify that conduction is the main transport phenomenon. This was done to make sure that installation errors and adhesive performance in vacuum were not manifesting change in the recorded waveforms.

Figure 10:
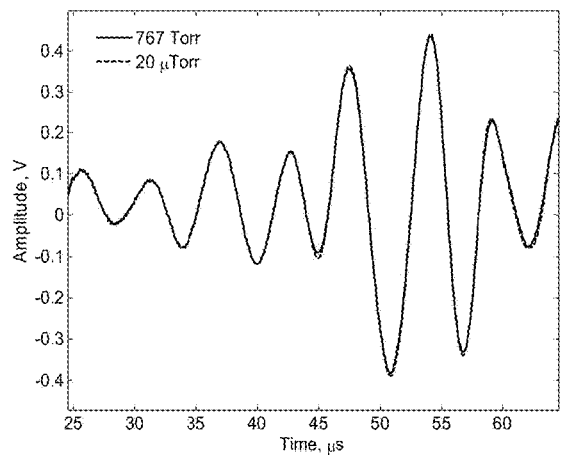
FIG. 10 is a graph showing the measured Lamb Wave in atmosphere and vacuum.

For SHM testing, a Ritec set-up like that shown in FIG. 9 is used to transmit elastic waves through the specimen via the bonded PWAS 22, 122. In one particular procedure, five tone burst sine waves were transmitted over a range of frequencies (250-350 kHz) and the responsive function was windowed for analysis based on the first pressure and shear wave arrival times. Of course, the scope of the present invention is not limited to any one particular regime for conducting SHM testing, and the foregoing example is exemplary only. Using such SHM techniques, FIG. 10 shows two measured waveforms that are plotted together, representing guided wave responses under atmospheric pressure (767 Torr) and under vacuum (2e-5 Torr). No clear distinction can be made to distinguish one measurement from another—the plots track one another substantially identically. From this, the inventors concluded that no acoustic energy is leaking into the gas medium surrounding the part while not under vacuum conditions.

Next, an interface, as shown in FIGS. 1-8, was introduced to demonstrate propagation of acoustic energy across an interface in atmosphere and in vacuum. The joint was connected with two ¼ in. bolts 16 with washers on each side of the structure or specimen. Torque was applied initially to 10 in-lbs to simulate a low stiffness joint and after all measurements the torque was released and reloaded to 500 in-lbs to create a highly stiffened interface. Results show the same overlap observed in prior testing for atmosphere and vacuum tests, meaning that the two plots at 10 in-lbs closely track one another, and the two plots at 500 in-lbs closely track one another, as shown in FIG. 11. Additionally, waveform differences are noticeable for each torque load. Based on the theory of acousto-elasticity, it is expected that both amplitude and phase will change based on the orientation and magnitude of applied stress with respect to Lamb wave propagation. These features can be measured to evaluate interface parameters. This is explained to show that it can be used to examine the conductive characteristics of a joint and does not require the need of vacuum to perform measurements.

Based on these preliminary tests, further testing was initiated. The two test specimens or structures 10, 110 were clamped to the cold plate at 18, 118 inside of the bell jar vacuum system (not shown). Thermocouples, PWAS, and patch heaters were wired through the bell jar system to their respective controllers. The refrigerated bath was turned on and set to run at 10° C. The power supply to the patch heaters was also turned on and set to provide 4.695 W of heat to each test specimen. This was done with the top of the bell jar vacuum system open and rotated away from the test specimens such that they were exposed to the ambient conditions within the room. Each specimen was then allowed to reach thermal equilibrium. In open air conditions this took approximately 20 minutes.

For this procedure, each specimen was determined to be at thermal equilibrium when the change in temperature of the specimen was less than 1° C. in a 10 minute time frame. For the open air tests, this determination was relaxed somewhat, as it was found by the inventors that the room temperature fluctuated by roughly 2° C. every 25 minutes. This fluctuation did not appear to have any effect on the closed to air or vacuum tests performed later. Once both specimens had reached thermal equilibrium, in open-to-air conditions, thermocouple temperature readings were recorded and PWAS data was taken at a range of frequencies, using a set-up like that shown in FIG. 9, and conducted in a manner like that described above.

This procedure was repeated with the bell jar closed but at atmosphere (mitigating the effects of the circulating air in the room) and under vacuum (below roughly 9E-5 Torr). The procedure was repeated with bolt torques of 0, 10, 30, and 50 in-lbs torque as shown in Table 1 (FIG. 12).

Figure 13:
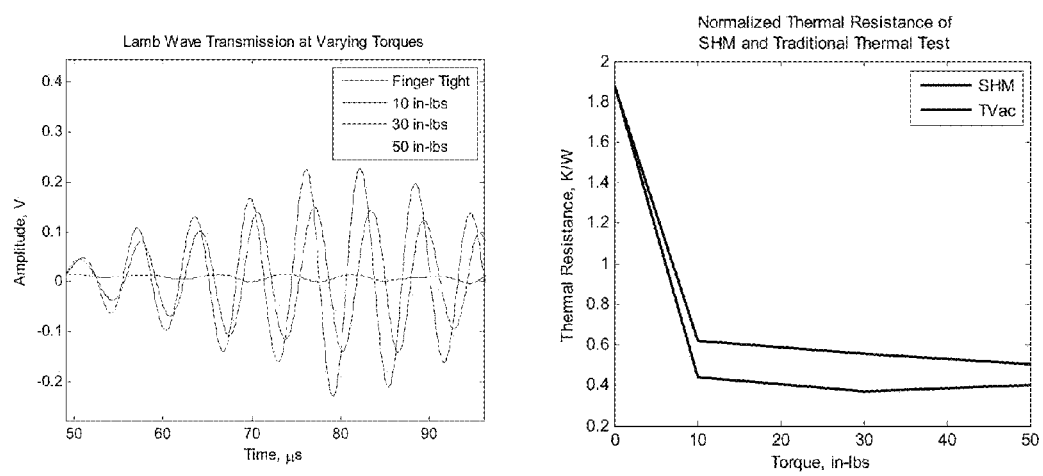
FIG. 13 is a pair of graphs illustrating the measured waveforms in vacuum and the normalized derived thermal resistance of SHM and TVac results for procedures conducted in accordance with the principles of the present invention.

FIG. 13 shows the waveforms of guided waves across a flanged joint and how the signal changes with increased torque (0 to 50 in-lbs.). These plots were originally in color, so are more difficult to discern in black and white as shown in FIG. 13. However, the specifics are not essential to understanding the claimed invention, and the plots in this application are provided for background information only. Generally speaking, inspection shows that phase, amplitude, and overall signal shape change, depending upon applied torque. For clarification, viewing the left-hand plot showing amplitude as a function of time, it is noted that the substantially straight line plot which hovers just above 0 on the amplitude axis as a function of time, represents measurements taken with finger-tightened torque only. The plot having the greatest amplitude changes, both above and below zero amplitude, is at 30 in-lbs. Of the two remaining plots, prior to 70 μsec, the 50 in-lb plot has greater amplitude variations than the 10 in-lb plot, but after 70 μsec, this shifts so that the 10 in-lb plot shows greater amplitude variation than the 50 in-lb plot, though slightly delayed in time.

Figure 14:
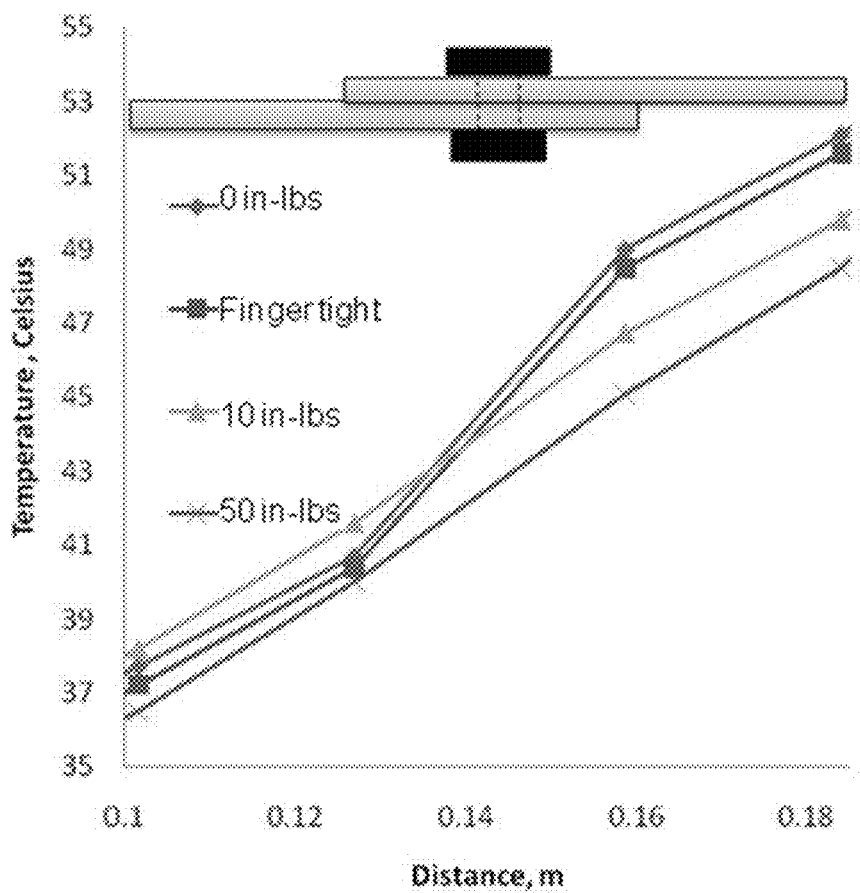
FIG. 14 is a plot showing thermal gradient data obtained from the testing performed by the inventors and described in this application.

FIG. 14 shows thermal gradient data, plotted as temperature vs. distance from the cold plate, and illustrated in conjunction with a schematic representation of the interface and associated structure which was studied. A plot line is presented for each of the torque levels discussed above in connection with FIG. 13. The data shows that increased torque results in predictably lower temperatures as a function of distance, as well as a straighter and more uniform plot line. Of course, this is indicative of improved and more uniform thermal conduction properties through the interface at higher bolt torque levels, because of greater and more consistent surface contact between the two joined structural members.

The amount of energy in each signal was then normalized with derived thermal resistances from thermal vacuum tests, as shown in the right-hand plot of FIG. 13. Results show a reasonable correlation of trends. One uncharacterized result is the increase in resistance after 30 in-lbs, which might be a result of deformation of the plates under bolted pressure, or a consequence of ultrasonic attenuation due to excessive loads and damping. This result does not impact the applicability of the inventors' invention, however.

The results achieved in the foregoing described testing show that ultrasonic measurements for evaluating thermal conductivity changes across structural interfaces for space systems, in normal atmospheric conditions, may be used as an alternative to thermal testing under vacuum conditions, as is currently the state of the art, since they have been found by the inventors to be limited to conductive energy transfer regardless of the presence of atmosphere. This extends the heretofore known applications of SHM evaluation, for evaluating structural characteristics of an interface, to infer characteristics of non-structural features of an interface, i.e. its thermal conductivity. There are at least two primary advances of this type of method over traditional testing, as described above. First, is the time needed to take a measurement. Thermal testing requires thermal gradients, accurate environmental conditions, and equilibrium. This process can potentially take weeks on a satellite. SHM measurements, on the other hand, can typically be made in seconds and require only an understanding of the current environmental conditions to properly isolate environmental influences in signals if necessary. The inventive methods are scalable as well, and their speed is limited only by the acquisition equipment. A second advantage is that testing with SHM does not require a thermal/vacuum chamber to remove the atmosphere to isolate conductive heat transfer from the system. All energy stays in the material due to impedance mismatching between the atmosphere and the solid surface, meaning measurements are the same on the launch pad as they are in the thermal chamber. This means that a quick test may be done at any time prior to or after launch to evaluate changes in thermal management of a system, and can be reasonably correlated to an area of interest for forensic analysis.

Thus, there are two primary advantageous processes which the inventors have developed for vastly improving the evaluation of changes in the thermal conductivity of structural interfaces in satellites and the like. The first process is for the purpose of establishing baseline values for a particular structural interface, or type of structural interface, as well as for establishing a correlation algorithm to relate ultrasonic transmission to thermal transmission, so that later testing can determine, in real time and on demand, whether substantial thermal conductivity changes have occurred in that interface or type of interface. The second process is for conducting that later testing, and then using the calculated algorithm and interface baseline values to determine thermal conductivity changes in a tested interface.

Now more particularly in reference to the first inventive process, the procedures described above in connection with FIGS. 1-13 are generally used to establish an experimentally-derived algorithm for converting SHM data changes to thermal conductivity changes across a particular structural joint or interface. More particularly, a particular jointed structure 10, 110 is instrumented with both PWAS 22, 122 and thermocouples 24, 124, as well as a patch heater 20, 120 and a cold plate 18, 118, or other equivalent sensing devices. In some instances, the structure 10, 110 may already be instrumented, for example, with PWAS 22, 122 for the purposes of SHM evaluations other than for detecting thermal conductivity changes. Once thermal equilibrium has been reached, as measured by the thermocouples 24, 124, a series of guided waves at varying frequencies are transmitted across the interface, using known SHM techniques, and PWAS wave propagation data is collected accordingly. This collected data is saved to establish a baseline for SHM data for that particular interface or type of interface and to determine the aforementioned algorithm for converting SHM data changes to thermal conductivity changes. Thermal conductivity data is collected at the same time, with the patch heater 20, 120 and cold plate actuated to establish desired temperatures, and using the thermocouples to measure temperature at predetermined locations, as noted above, along the distance between the heater and cold plate, extending across the interface. The two sets of data are used to derive the appropriate conversion algorithm for that particular interface or type of interface. In the event that the algorithm is already established, then a baseline value for SHM measurements taken across a particular joint can be established using wave propagation data generated by the PWAS along, without a need for instrumenting the structure to measure thermal conductivity.

Now more particularly in reference to the second inventive process, when it is desired to determine whether thermal conductivity changes have occurred in a particular structural interface, embedded PWAS 22, 122 are utilized in a method substantially similar to that described above, wherein guided waves are transmitted across the interface of interest, and data is collected from the PWAS. Once this data has been collected, changes in the data relative to the baseline data can be correlated to changes in thermal conductivity over that interface or an equivalent interface by applying the algorithm already calculated from the earlier testing data, related to the first inventive process.

While this invention has been described with respect to various specific examples and embodiments, it is to be understood that various modifications may be made without departing from the scope thereof. Therefore, the above description should not be construed as limiting the invention, but merely as an exemplification of preferred embodiments thereof and that the invention can be variously practiced within the scope of the following claims.

What is claimed is:

1. A method of using Structural Health Monitoring (SHM) techniques for determining whether changes in thermal conductivity have occurred to a particular interface between two joined structural members, the method comprising: sending a guided wave through a structure that contains at least two structural members joined at an interface, wherein the guided wave is transmitted across the interface; measuring the guided wave that has subsequently propagated through the structure and across said interface, thus obtaining a measured result; comparing the measured result to a baseline result previously obtained for the interface or a substantially equivalent interface, and calculating a quantitative difference between the measured result and the baseline result; and calculating a change in thermal conductivity across said interface which is equivalent to the quantitative difference between the measured result and the baseline result, using a predetermined algorithm stored in the memory.

2. The method as recited in claim 1, wherein the measuring step is performed using PWAS, which detect and transmit guided wave signals to a digitizer for processing.

3. The method as recited in claim 1, wherein a plurality of PWAS are disposed on each member of said structure for detecting guided wave signals.

4. The method as recited in claim 3, wherein said interface comprises a bolted joint.

5. A method of using Structural Health Monitoring (SHM) techniques for determining whether changes in thermal conductivity have occurred to a particular interface between two joined structural members, the method comprising: sending a guided wave through a structure that contains at least two structural members joined at an interface, wherein the guided wave is transmitted across the interface; measuring the guided wave that has subsequently propagated through the structure and across said interface, thus obtaining a first measured result; sending a second guided wave through the interface of said structure at a point substantially later in time than the first sending step; measuring the guided wave that has subsequently propagated through the structure and across said interface, thus obtaining a second measured result; comparing the second measured result to the first measured result and calculating a quantitative difference between the second measured result and the first measured result; and calculating a change in thermal conductivity across said interface which is equivalent to the quantitative difference between the second measured result and the first measured result, using a predetermined algorithm stored in the memory.

6. The method as recited in claim 5, wherein each measuring step is performed using PWAS, which detect and transmit guided wave signals to a digitizer for processing.

7. The method as recited in claim 5, wherein a plurality of PWAS are disposed on each member of said structure for detecting guided wave signals.

8. The method as recited in claim 7, wherein said interface comprises a bolted joint.

* * * * *